United States Patent
Carlson et al.

(10) Patent No.: US 11,978,539 B2
(45) Date of Patent: May 7, 2024

(54) SYSTEMS AND METHODS FOR MULTI-DOMAIN DATA SEGMENTATION, AUTOMATIC HYPOTHESES GENERATION AND OUTCOME OPTIMIZATION

(71) Applicant: Included Health, Inc., San Francisco, CA (US)

(72) Inventors: Eric Carlson, San Francisco, CA (US); Molong Li, San Francisco, CA (US); Zachary Taylor, San Francisco, CA (US); Carolina Marquez, San Francisco, CA (US)

(73) Assignee: Included Health, Inc., San Francisco, CA (US)

( * ) Notice: Subject to any disclaimer, the term of this patent is extended or adjusted under 35 U.S.C. 154(b) by 0 days.

(21) Appl. No.: 17/752,715

(22) Filed: May 24, 2022

(65) Prior Publication Data
US 2023/0386621 A1    Nov. 30, 2023

(51) Int. Cl.
*G16H 10/40* (2018.01)

(52) U.S. Cl.
CPC .................................. *G16H 10/40* (2018.01)

(58) Field of Classification Search
CPC .................................................. G16H 10/40
See application file for complete search history.

(56) References Cited

U.S. PATENT DOCUMENTS

| | | | |
|---|---|---|---|
| 2014/0129504 A1* | 5/2014 | Soon-Shiong | G06N 5/04 706/47 |
| 2014/0232631 A1* | 8/2014 | Fleischmann | G06K 9/6255 345/156 |
| 2015/0356486 A1* | 12/2015 | Alhimiri | G16H 20/10 705/2 |
| 2017/0068789 A1* | 3/2017 | Dalton | G16H 50/20 |
| 2017/0180554 A1* | 6/2017 | McCormack | H04M 3/5175 |
| 2018/0018436 A1* | 1/2018 | Opitz | G06F 16/2474 |

(Continued)

OTHER PUBLICATIONS

Edward H. Shortliffe, "Biomedical Informatics", 2014, pp. 1-965 (Year: 2014).*

*Primary Examiner* — Rajesh Khattar
*Assistant Examiner* — Steven G. S. Sanghera
(74) *Attorney, Agent, or Firm* — Finnegan, Henderson, Farabow, Garrett & Dunner LLP (57) ABSTRACT

Methods, systems, and computer-readable media for multi-domain, multi-modal data segmentation, and automatically generating and refining hypotheses. The method receives data from a plurality of data sources; synthesizing the receive data; identifying trigger event data based on the synthesized data; generating an episode based on a segmentation of the synthesized data and trigger event data; and identifying at least one set of observational features associated with the episode based on the synthesized data and a relevancy metric. The method also includes iteratively generating a hypothesis based on the observational features using machine learning, predicting an outcome based on the hypothesis using machine learning, generating an outcome measure, and validating the hypothesis based on the outcome measure. The method also includes determining an optimal hypothesis upon reaching the threshold value; analyzing coefficients associated with the optimal hypothesis; and identifying a set of factors associated based on the analyzed coefficients.

12 Claims, 8 Drawing Sheets

(56) References Cited

U.S. PATENT DOCUMENTS

| | | | |
|---|---|---|---|
| 2020/0126641 A1* | 4/2020 | Li | G16H 10/00 |
| 2021/0193302 A1* | 6/2021 | Day | G06Q 10/0631 |
| 2021/0312309 A1* | 10/2021 | Yamamoto | G06N 5/041 |
| 2022/0129794 A1* | 4/2022 | McGrath | G06F 16/2379 |
| 2022/0188349 A1* | 6/2022 | Kochura | G06N 20/00 |

* cited by examiner

SYSTEMS AND METHODS FOR MULTI-DOMAIN DATA SEGMENTATION, AUTOMATIC HYPOTHESES GENERATION AND OUTCOME OPTIMIZATION

BACKGROUND

An ever-increasing amount of data and data sources are now available to researchers, analysts, organizational entities, and others. This influx of information allows for sophisticated analysis but, at the same time, presents many new challenges for sifting through the available data and data sources to locate the most relevant and useful information. As the use of technology continues to increase, so, too, will the availability of new data sources and information.

Because of the abundant availability of data from a vast number of data sources, determining the optimal values and sources for use presents a complicated problem difficult to overcome. Accurately and fully utilizing the available data across multiple sources can require both a team of individuals possessing extensive domain expertise as well as many months to years of work to evaluate the outcomes. The process can involve exhaustively searching existing literature, publications, and other available data to identify and study relevant data sources that are available both privately and publicly.

While this approach may sometimes provide effective academic analysis, applying these types of analytical techniques to domains requiring accurate results obtainable only through time and resource intensive research is incompatible with modern applications' demands. For example, the developed process for evaluating outcomes may not line up with specific circumstances or individual considerations. In this scenario, applying the process requires extrapolation to fit the specific circumstances, to dilute the process's effectiveness, or to require spending valuable time and resources to modify the process. As a result, processes developed in this way typically provide only generalized guidance insufficient for repurposing in other settings or by other users. As more detailed and individualized data becomes available, demand for the ability to accurately discern relevant data points from the sea of available information across multiple data sources, and efficiently apply that data across myriads of personalized scenarios increases.

SUMMARY

Certain embodiments of the present disclosure relate to a non-transitory computer readable medium including instructions that are executable by one or more processors to cause a system to perform a method for multi-domain data segmentation, and automatically generating and refining hypotheses. The method may include receiving data from a plurality of data sources; synthesizing the receive data; identifying a trigger event based on the synthesized data; generating an episode based on a segmentation of the synthesized data and trigger event; and identifying at least one set of observational features associated with the episode based on the synthesized data. The method may also include iteratively performing operations until a threshold value has been reached, wherein the operations comprise: generating a hypothesis based on the observational features using machine learning, generating a measure of one or more outcomes, and validating the hypothesis based on the generated measures. The method may also include identifying one or more driving factors for the one or more outcomes using an optimal hypothesis.

According to some disclosed embodiments, the data sources may comprise claims data, digital product data, telephonic data, or laboratory data.

According to some disclosed embodiments, synthesizing the received data may further comprises capturing data.

According to some disclosed embodiments, the instructions may further comprise normalizing the data.

According to some disclosed embodiments, the trigger event may comprise a clinical visit, a claim filing, or a telephone encounter.

According to some disclosed embodiments, the outcomes metric may comprise a provider match, a concierge referral, or monetary savings.

According to some disclosed embodiments, the outcomes metric comprises potential savings, reduction in expenditure, or other product metrics.

According to some disclosed embodiments, the method may further comprise generating a set of recommendations based on the identified set of factors and outputting the recommendations through a set of outflow channels.

According to some disclosed embodiments, the set of outflow channels comprise customers, product and service staff, user interfaces, and digital agents.

Other systems, methods, and computer-readable media are also discussed within.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION

In the following detailed description, numerous specific details are set forth in order to provide a thorough understanding of the disclosed example embodiments. However, it will be understood by those skilled in the art that the principles of the example embodiments may be practiced without every specific detail. Well-known methods, procedures, and components have not been described in detail so as not to obscure the principles of the example embodiments. Unless explicitly stated, the example methods and processes described herein are neither constrained to a particular order or sequence nor constrained to a particular system configuration. Additionally, some of the described embodiments or elements thereof can occur or be performed simultaneously, at the same point in time, or concurrently. Reference will now be made in detail to the disclosed embodiments, examples of which are illustrated in the accompanying drawings. Unless explicitly stated, sending and receiving as used herein are understood to have broad meanings, including sending or receiving in response to a specific request or without such a specific request. These terms thus cover both active forms, and passive forms, of sending and receiving.

The embodiments described herein provide technologies and techniques for evaluating large numbers of data sources and vast amounts of data used in the creation of a machine learning model. These technologies can use information relevant to the specific domain and application of a machine learning model to prioritize potential data sources. Further, the technologies and techniques herein can interpret the available data sources and data to extract probabilities and outcomes associated with the machine learning model's specific domain and application. The described technologies can synthesize the data into a coherent machine learning model, which can be used to analyze and compare various paths or courses of action.

These technologies can efficiently evaluate data sources and data, prioritize their importance based on domain and circumstance specific needs, and provide effective and accurate predictions that can be used to evaluate potential courses of action. The technologies and methods allow for the application of data models to personalized circumstances. These methods and technologies allow for detailed evaluation that can improve decision making on a case-by-case basis. Further, these technologies can evaluate a system where the process for evaluating outcomes of data may be set up easily and repurposed by other uses of the technologies.

Technologies may utilize machine learning models to automate the process and predict responses without human intervention. The performance of such machine learning models is usually improved by providing more training data. A machine learning model's prediction quality is evaluated manually to determine if the machine learning model needs further training. Embodiments of these technologies described can help improve machine learning model predictions using the quality metrics of predictions requested by a user.

Figure 1A:
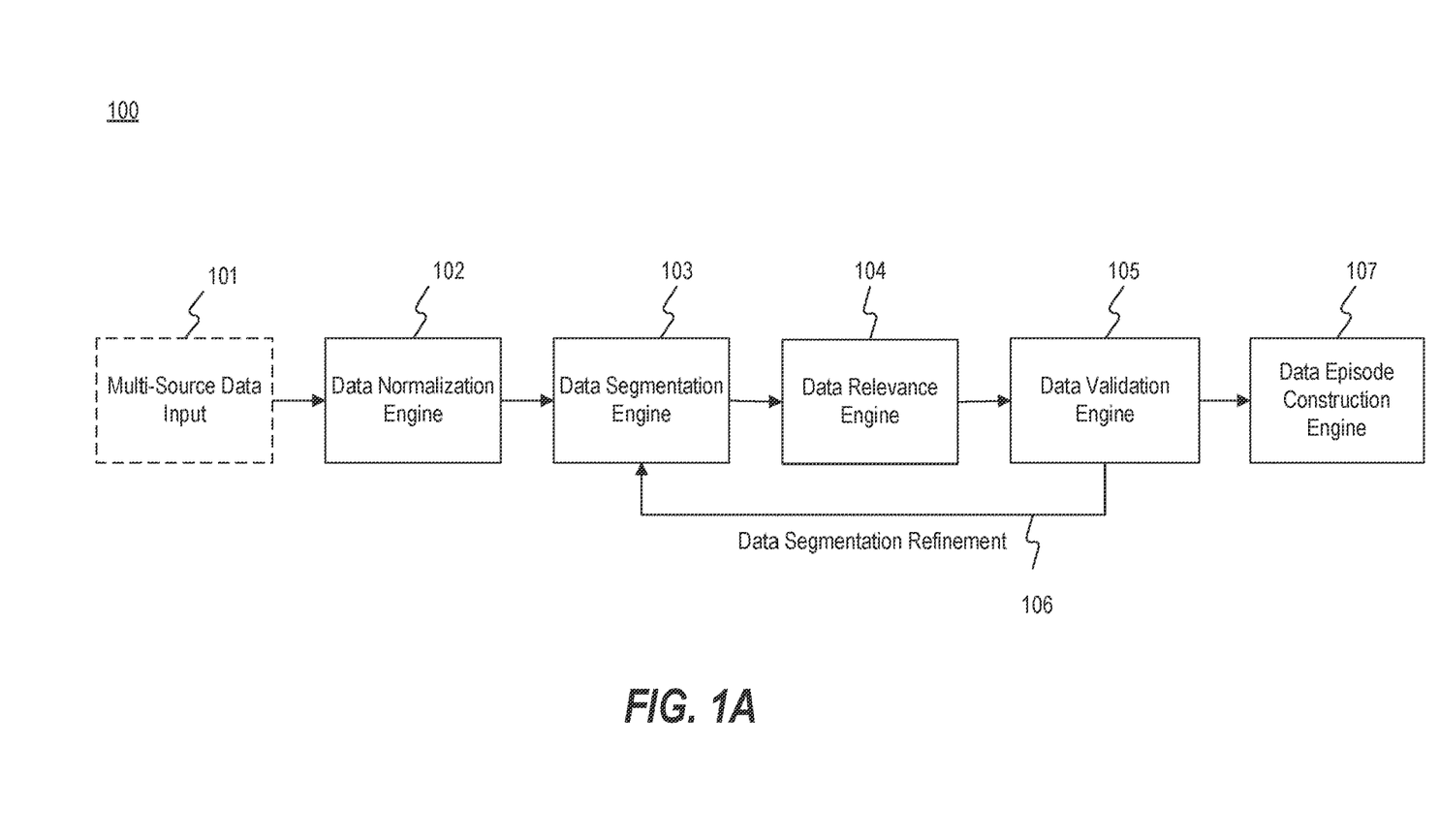
FIG. 1A is a block diagram illustrating various exemplary components of a system for generating and refining data episodes based on data input from multiple data sources, according to some embodiments of the present disclosure.

FIG. 1A is a block diagram illustrating various exemplary components of a system 100 for generating and refining data episodes based on data input from multiple data sources, according to some embodiments of the present disclosure. System 100 may include multi-source data input 101 from multiple data sources, data normalization engine 102, data segmentation engine 103, data relevance engine 104, data validation engine 105, and data episode construction engine 107.

As shown in FIG. 1A, system 100 may receive multi-source data input 101 from multiple data sources as input. In some embodiments, the multiple data sources may include, but are not limited to, data from multiple domains or modalities. For instance, in a healthcare setting, the data sources may comprise, but are not limited to, claims data, digital product data, telephonic call center data, or laboratory data.

In some embodiments, system 100 may include data normalization engine 102. Data normalization engine 102 may perform synthesis of data across multiple data sources. In some embodiments, data normalization engine 102 may synthesize data into collections of canonical data tables. In some embodiments, a canonical table may include one or more multiple data fields. Data fields may include, but are not limited to, a user identification ID, a location ID, a time ID, a data category, an event ID, or an event description. In some embodiments, data normalization engine 102 may also synthesize data by capturing data from additional data sources. An additional data source may include, but is not limited to, an external database. In some embodiments, data normalization engine 102 may perform normalization of the synthesized data. In some embodiments, data normalization engine 102 may perform data normalization based on data fields of canonical tables. In some embodiments, data normalization engine 102 may perform data normalization based on natural language processing modules. In some embodiments, natural language processing modules may include, but are not limited to, a labelling module, or a data processing module. Data normalization engine 102 may perform data normalization based on one or more corpus databases. Data normalization engine 102 may perform data normalization based on a machine learning platform.

According to some embodiments, data segmentation engine 103 may segment the synthesized data from multiple data sources. Data segmentation engine 103 may segment the synthesized data into one or more data collections. Data segmentation engine 103 may segment the data based on one or more pre-defined trigger events. In some embodiments, a trigger event may comprise of a data event or data point defined across one or more data sources. For instance, in a healthcare setting, a trigger event may comprise of, but is not limited to, an event at a specific point in time, such as a search for a new provider physician, a search for a concierge referral, a clinical visit, or a telephonic encounter for medical care. In some embodiments, data segmentation engine 103 may perform data segmentation by selecting, within the synthesized data, one or more data collections within a specific timespan associated with the trigger event. In some embodiments, data segmentation engine 103 may select data within a specific timespan based on the time stamp of the trigger event. In some embodiments, trigger event data may comprise of data associated with a time stamp and a trigger event. In some embodiments, data segmentation engine 103 may receive instructions from data validation engine 105 to perform data segmentation refinement, which will be described later in detail. Data segmentation engine 103 may perform data segmentation refinement by performing a segmentation of the synthesized data, which is different from its previous data segmentation of the synthesized data.

According to some embodiments, data relevance engine 104 may identify a set of observations or events across multiple data sources, which may be relevant to a segmented data collection based on a trigger event. For instance, in a health care setting, if the trigger event comprises a patient who is seeking to undergo knee surgery, an observation or event could comprise, but is not limited to, previous individualized recommendations of knee surgeons to the patient based on his/her medical needs or insurance coverage, previous claims or episodes of care associated with the patient, past outreach efforts to the patient with regard to appointment adherence or healthcare education, telephonic patient encounters or emergency medical encounters relating to previous knee-related symptoms. In some embodiments, data relevance engine 104 may identify the set of observations or events based on a relevancy metric. In some embodiments, the relevancy metric may comprise of the time proximity of the observation or event to the trigger event associated with the segmented data collection. In some embodiments, the relevancy metric may comprise of the similarity between the category or type of the observation or event to the trigger event.

According to some embodiments, data validation engine 105 may validate the segmented data collection by measuring the efficacy of a segmented data collection. In some embodiments, data validation engine 105 may perform an efficacy measurement based on an efficacy metric. In some embodiments, an efficacy metric may be based on a sufficiency value of the number of data events within the segmented data collection. In some embodiments, an efficacy metric may be based on the time proximity of the data events within the segmented data collection. In some embodiments, an efficacy metric may be based on the type of trigger event associated with the segmented data collection. In some embodiments, if data validation engine 105 determines that the efficacy of a segmented data collection is below a specific threshold value, it may transmit instructions 106 to data segmentation engine 103 to perform a data segmentation refinement. In some embodiments, data validation engine 105 may measure the efficacy of the refined segmented data collection. In some embodiments, data validation engine 105 may perform iterative cycles of data segmentation refinement and efficacy measurement until the measured efficacy of the refined data segmentation reaches a specific threshold value. In some embodiments, a threshold value may be set automatically or based on user input.

According to some embodiments, data episode construction engine 107 may aggregate the trigger event and the set of observations or events associated with a segmented data collection into a data episode. In some embodiments, a data episode comprises of a trigger event and a set of observations or events associated with the trigger event based on a determination by the data relevance engine 104. In some embodiments, data episode construction engine 107 may store the data episode in a data episode configuration file. In some embodiments, data episode construction engine 107 may transmit data episodes to a machine learning engine for additional analysis. In some embodiments, a machine learning engine may be exemplified by machine learning engine 214 in FIG. 2.

Figure 1B:
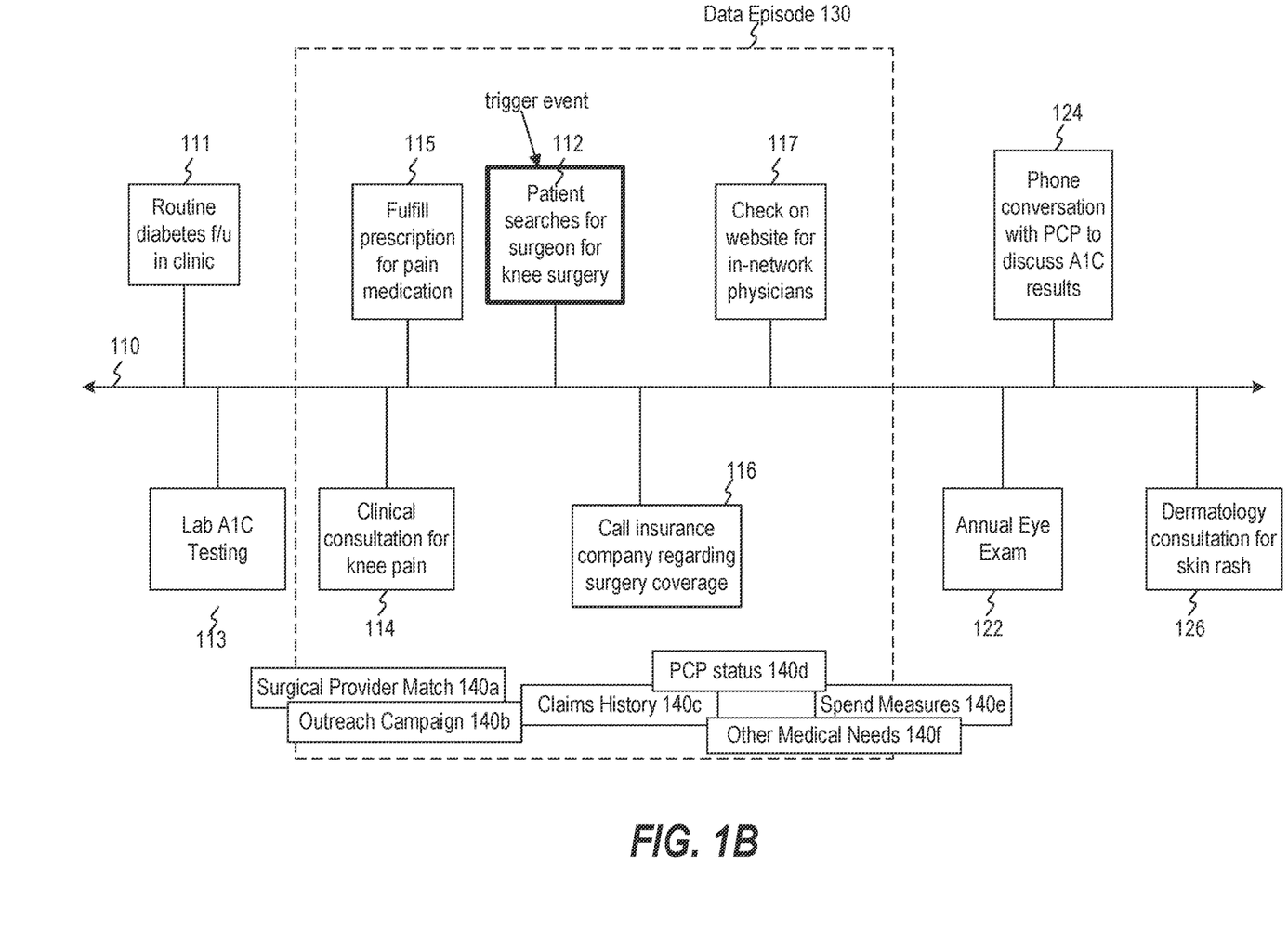
FIG. 1B is a diagram illustrating an exemplary data episode in a healthcare setting, comprising a trigger event and a set of observations or events associated with the data episode, according to some embodiments of the present disclosure.

FIG. 1B is a diagram illustrating an exemplary data episode 130 in a healthcare setting, comprising a trigger event 112 and a set of observations or events (140a-f) associated with the data episode, according to some embodiments of the present disclosure. It will be noted that FIG. 1B will be described referring to FIG. 1A for illustration purposes. In FIG. 1B, a user of the current system may be exemplified by a patient in a healthcare setting. The patient's healthcare data may be represented chronologically in a timeline as exemplified by timeline 110. In timeline 110, patient data may comprise data from multiple sources, which may have been synthesized and normalized by data normalization engine 102. In some embodiments, data segmentation engine 103 may identify a trigger event 112, such as the patient searching for a surgeon to perform his knee surgery. Data segmentation engine 103 may perform data segmentation based on the trigger event and a specific timespan associated with the trigger event. For instance, a specific timespan associated with trigger event 112 may comprise the time frame before or after the trigger event within a certain length of time (e.g., within 3 months). In other embodiments, a specific timespan associated with trigger event 112 may comprise the time frame spanning from the occurrence of at least one data event preceding the trigger event (e.g., clinical consultation for knee pain 114, which precedes the trigger event of searching for a knee surgeon 112), to the occurrence of at least one data event following the trigger event (e.g., call insurance company regarding surgery coverage 116, which follows trigger event 112). Based on the trigger event and time frame, data segmentation engine 103 may segment the patient data such that it would include all data events within the time frame. For instance, in FIG. 1B, data events which may be included in the data segmentation includes, such as, clinical consultation for knee pain 114, fulfill prescription for pain medication 115, call insurance company regarding surgery coverage 116, or check on website for in-network physicians 117. Data segmentation engine 103 may segment the data such that it would exclude data events not directly associated with the trigger event 112 or outside of a specific time frame associated with trigger event 112, such as, routine diabetes f/u in clinic 111, Lab A1C testing 113, annual eye exam 122, phone conversation with PCP to discuss A1C results 124, or dermatology consultation for skin rash 126.

In some embodiments, data relevance engine 104 may identify a set of observations or events associated with the data segmentation. For instance, in FIG. 1B, exemplary observations or events associated with the data segmentation based on the trigger event 112 may include surgical provider match 140a, outreach campaign 140b, claims history 140c, PCP status 140d, spend measure 140e, or other medical needs 140f. In some embodiments, data relevance engine 104 may identify the set of observations or events based on a relevancy metric. In some embodiments, the relevancy metric may comprise of the time proximity of the observation or event to the trigger event associated with the segmented data collection. In some embodiments, the relevancy metric may comprise of the similarity between the category or type of the observation or event to the trigger event. As described in FIG. 1A, data validation engine 105 may validate the data segmentation by measuring the efficacy of a segmented data collection. Here, as exemplified by FIG. 1B, data episode construction engine 107 may aggregate the trigger event 112 and the set of observations or events 140a-f associated with the data segmentation into a data episode 130.

Figure 2:
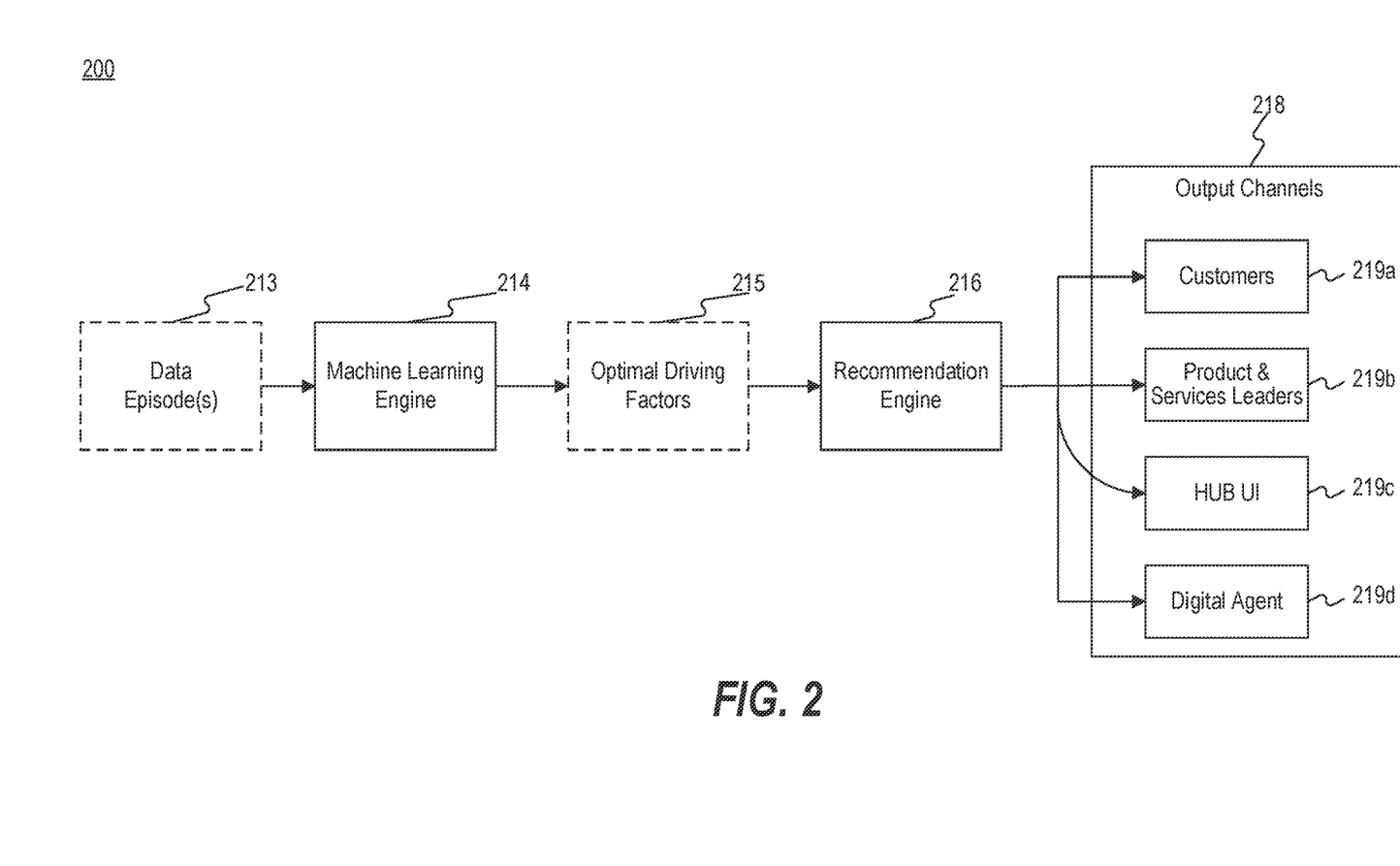
FIG. 2 is a block diagram illustrating exemplary components of a system for determining optimal driving factors and generating personalized recommendations for a data episode, according to some embodiments of the present disclosure.

FIG. 2 is a block diagram illustrating exemplary components of a system 200 for determining optimal driving factors and generating recommendations for a data episode, according to some embodiments of the present disclosure. According to some embodiments, system 200 may include machine learning engine 214, recommendation engine 216, and output channels 218.

As shown in FIG. 2, system 200 may receive one or more data episodes 213. In some embodiments, data episode(s) 213 can be acquired from data episode construction engine 107 of FIG. 1A.

According to some embodiments, machine learning engine 214 may analyze one or more data episodes 213 using one or more machine learning models. Machine learning engine 214 may be trained using machine learning training engine, as exemplified by engine 310 in FIG. 3A. Machine learning engine 214 may be configured to predict a set of optimal driving factors based on the data episode(s)

acquired as input. In some embodiments, an optimal factor may be an observation selected from the set of observations associated with an optimal hypothesis generated during training and may be exemplified by machine learning training engine 310. For instance, in a healthcare setting, machine learning engine 214 may determine that the set of optimal driving factors, which are associated with one or more desired outcomes, may comprise patient's insurance coverage, patient's previous selection of physicians, healthcare outreach efforts targeted toward the patient (e.g., via email, phone, or an online patient portal), etc. Machine learning engine 214 may determine the set of optimal driving factors 215 based on the set of observations or events associated with an optimal hypothesis.

According to some embodiments, recommendation engine 216 may generate recommendations based on a set of optimal driving factors 215. In some embodiments, for instance in a healthcare setting, if an optimal driving factor is associated with outreach efforts targeted toward a patient, then recommendation engine 216 may generate recommendations based on this optimal driving factor to increase the frequency or types of outreach efforts toward the patient. If an optimal driving factor is associated with the cost saving, recommendation engine 216 may generate recommendation based on this optimal driving factor to recommend a cost-efficient treatment or surgical provider. In some embodiments, recommendation engine 216 is configured to generate recommendation(s) based on multiple driving factors. In some embodiments, the generated recommendations may be personalized to target specific users of the system. In some embodiments, the generated recommendations are based on one or more outcomes from the set of measured outcomes.

According to some embodiments, recommendation engine 216 may utilize output channels 218 to output recommendations. In some embodiments, a channel may be utilized by engine 216 to transmit data based on recommendations generated by engine 216 to one or more specific users or systems. In some embodiments, for instance, output channels 218 may comprise Customers channel 219a, Product & Service Leaders channels 219b, HUB User Interface (UI) 219c, or Digital Agent channel 219d. In some embodiments, recommendation engine 216 may output recommendations via digital media as exemplified by a web interface or a mobile phone interface. Recommendation engine 216 may output recommendations through telephone calls or printed personalized informational materials to the user.

Figure 3A:
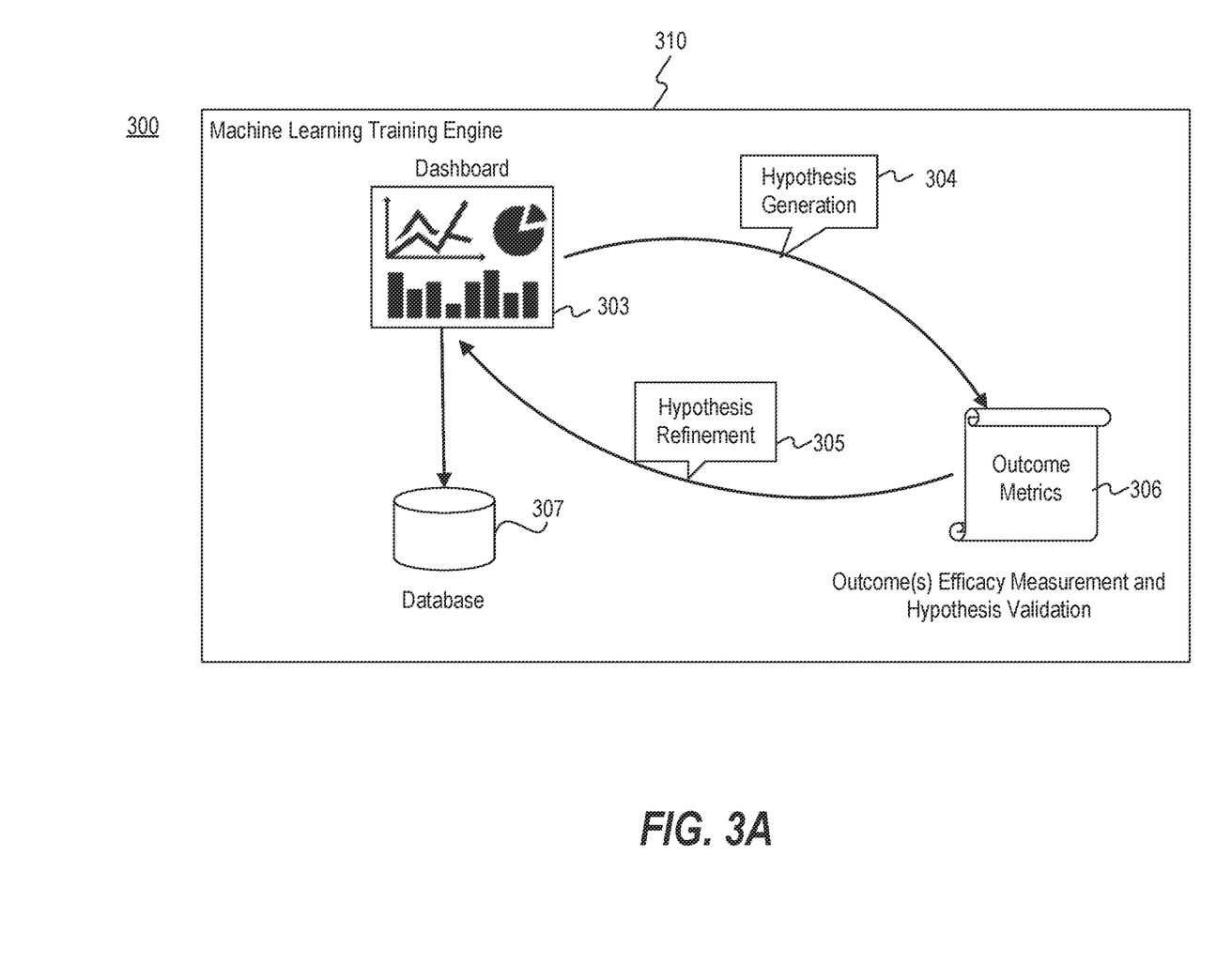
FIG. 3A is a diagram illustrating an exemplary process for hypotheses generation and refinement based on outcomes assessments using machine learning, according to some embodiments of the present disclosure.

FIG. 3A is a diagram illustrating an exemplary process 300 for hypothesis generation and refinement used during machine learning training engine 310, according to some embodiments of the present disclosure. Machine-learning training engine 310 may comprise dashboard 303. In some embodiments, dashboard 303 may comprise a user interface which allows a user to specify a hypothesis associated with a data episode. In some embodiments, machine-learning training engine 310 may automatically generate a hypothesis associated with a data episode as exemplified by hypothesis generation 304. In some embodiments, the hypothesis may comprise of a subset of observations or events within the set of observations or events associated with the data episode. Machine-learning training engine 310 may retrieve one or more outcomes of interest associated with the hypothesis. In some embodiments, the one or more outcomes may be retrieved from an external system or data source. For instance, in the healthcare setting, an outcome may be exemplified by clinical outcomes, success of treatment, monetary savings by the patient, patient's selection and engagement of a healthcare provider based on a recommended provider match, or total market shares captured. Engine 310 may display the generated hypothesis on dashboard 303. In some embodiments, a user may define a hypothesis using dashboard 303. In some embodiments, engine 310 may store the generated hypothesis in a data structure or database 307.

Machine-learning training Engine 310 may measure the efficacy of the one or more outcomes based on one or more outcome metrics as exemplified by outcomes metrics 306. In some embodiments, for instance, in a healthcare setting, an outcome metric may be exemplified by the positive nature of the clinical outcome, the amount of monetary savings by the patient, the amount of total market shares captures, or the rate of patient's actual engagement with a recommended healthcare provider. In some embodiments, an outcome metric may be based on a metric for an external system or product. Machine-learning training engine 310 may validate the hypothesis by comparing the efficacy of one or more outcomes associated with the hypothesis with a threshold value. Machine-learning training engine 310 may determine when an outcome efficacy is below the threshold value. Machine-learning training engine 310 may refine a hypothesis when an outcome efficacy is below threshold value as exemplified by 305. Machine-learning training engine 310 may perform hypothesis refinement by automatically generating an alternative hypothesis based on a different subset of observations or events within the set of observations or events associated with the data episode. Machine-learning training engine 310 may also perform hypothesis refinement based on hypothesis inputted by the user via the dashboard 303. Machine-learning training engine 310 may validate the alternative hypothesis based on one or more efficacy outcome measures. Machine-learning training engine 310 may perform iterative cycles of hypothesis generation, validation, and refinement until an efficacy outcome measure for a hypothesis reaches the threshold value. In some embodiments, machine-learning training engine 310 may identify an optimal hypothesis based on a hypothesis which has an efficacy outcome measure that is equal to or above the threshold value. The threshold value may be specified by a user or determined automatically. Machine-learning training engine 310 is trained to determine a set of optimal driving factors associated with the one or more measured outcomes. Machine-learning training engine 310 can be trained to predict or determine the set of optimal driving factors based on the set of observations or events associated with the optimal hypothesis.

Figure 3B:
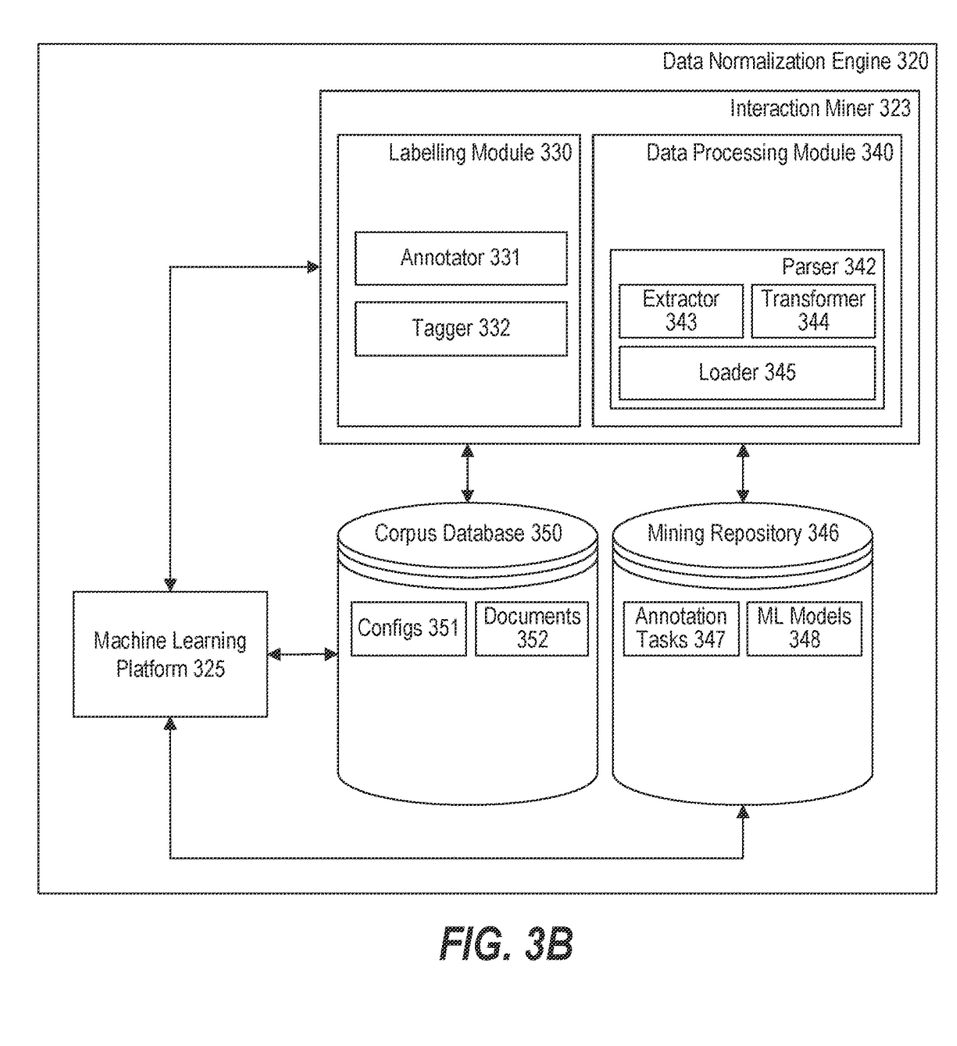
FIG. 3B is a block diagram illustrating various exemplary components of a data normalization engine comprising natural language processing modules, according to some embodiments of the present disclosure.

FIG. 3B is a block diagram illustrating various exemplary components of a data normalization engine 320 comprising natural language processing modules, according to some embodiments of the present disclosure. As illustrated in FIG. 1A, a data normalization engine may interact with data from multiple data sources 101 to perform data normalization. For instance, in a healthcare setting, data normalization engine 320 may normalize speech data pertaining to a patient's telephonic medical encounter, or specialized claims data into a canonical data format. In FIG. 3B, data normalization engine 320 may normalize data based on natural language processing modules. In some embodiments, natural language processing modules may include, but are not limited to, a labelling module 330, or a data processing module 340. Data normalization engine 320 may perform data normalization based on one or more corpus databases as exemplified by 350, or a mining repository as exemplified by 346.

Data normalization engine 320 may include interaction miner 323 to determine labels to associate with multi-source data 101. Data normalization engine 320 may use additional configuration details. Interaction miner 323 may include labeling module 330 and data processing module 340 to determine labels. Interaction miner 323 may use corpus database 350 to store and access various labels of multi-source data 101. Interaction miner 323 may use mining repository 346 to get the definitions of tasks and models to generate labels. Interaction miner 323 works with machine learning model platform 325, corpus database 350, and mining repository 346 to generate labels and semi-supervised and unsupervised.

Data normalization engine 320 may also include Machine Learning (ML) platform 325 to help determine labels to associate with multi-source data 101. Interaction miner 323 and ML model platform 325 may access data and configurations in corpus database 350 and mining repository 346 to generate labels to determine insights.

Labeling module 330 may aid in labeling input data retrieved from data sources such as multi-source data 101. Labeling module 330 may store parts of the retrieved input data from multi-source data 101 along with generated labels in corpus database 350. Labeling module 330 may include manual processing of input data using annotator 331 and automatic and real-time processing of input data from multi-source data 101 using tagger 332 to generate labels. In some embodiments, labeling module 330 may be configured to generate different labels and types of labels for matching data. Configurations may include configurations for annotator 331 and tagger 332 and stored in corpus database 350.

Annotator 331 may help annotate multi-source data 101 by providing a list of annotations to use with the content in multi-source data 101. Annotator 331 may be configured to include the list of annotations to process with a list of annotators. Annotator 331 may receive a configuration (e.g., from a configuration file) over a network (not shown). The configuration file may be a text file or a structured document such as a YAML or JSON. In some embodiments, the configuration file may include a list of documents or a database query to select the list of documents. In some embodiments, a list of documents may be presented as a regex formula to match a set of documents. The configuration file may include additional details for annotations in mining repository 346.

Tagger 332 may automatically tag data with labels using machine learning (ML) model platform 325. Data Normalization Engine 320 may train tagger 332 using data annotated with labels provided by annotator 331. In some embodiments, tagger 332 may be used with unstructured data and need auto labeling of the data.

Data processing module 340 takes as input multi-source data 101 and labels provided by annotator 331 and tagger 332 to generate insights about the contents of data 132. In some embodiments, insights may represent potential interactions between two or more labelled entities within the data. Data processing module 340 may store the insights in corpus database 350. Data processing module 340 may include aggregator 341 to help combine various interaction parts in the data to generate insights.

Parser 342 may retrieve data from various data sources (e.g., multi-source data 101) and process the data to documents 352 so that it may be used with the remainder of data normalization engine 320. Parser 342 may further include extractor 343, transformer 344, and loader 345 modules. Extractor 343 and transformer 344 may work together to generate documents 352 and other data in corpus database 350. Transformer 344 may connect the disparate data extracted from data sources 101 by extractor 343 and store it in corpus database 350.

Extractor 343 may retrieve input data from multi-source data 101, and each of these data sources may represent a different type of data source. For instance, in a healthcare setting, a data source may represent structured data such as hierarchical topics selected by a service provider communicating with a user or a usage log of a service by a user. In some embodiments, data sources may be flat files, such as call and chat transcripts. Further, data sources may contain overlapping or completely disparate data sets. In some embodiments, a data source may contain information about a user usage log of a service. In contrast, other data sources may contain various disparate topics a user discussed with a service provider. Extractor 343 may interact with the various data sources, retrieve the relevant data, and provide that data to transformer 344.

Transformer 344 may receive data from extractor 343 and process the data into standard formats. In some embodiments, transformer 344 may normalize data such as dates. For example, a data source for a service usage log may store dates in a day-month-year format, while a data source for chat transcripts may store dates in a year-month-day format. In this example, transformer 344 may modify the data provided through extractor 343 into a consistent date format. Accordingly, transformer 344 may effectively clean the data provided through extractor 343 so that all of the data, although originating from a variety of sources, has a consistent format. For example, usage data may include a user ID of a user, but a chat transcript may include the full name of the same user. In the second example, transformer 344 may include the missing full name in a usage log of a service.

Moreover, transformer 344 may extract additional data points from the data sent by extractor 343. For example, transformer 344 may process a date in a year-month-day format by extracting separate data fields for the year, the month, and the day. Transformer 344 may also perform other linear and non-linear transformations and extractions on categorical and numerical data, such as normalization and demeaning. Transformer 344 may provide the transformed or extracted data to loader 345. In some embodiments, transformer 344 may store the transformed data in corpus database 350 for later use by loader 345 and other components of interaction miner 323.

Loader 345 may receive normalized data from transformer 344. Loader 345 may merge the data into varying formats depending on the specific requirements of data normalization engine 320 and store the data in an appropriate storage mechanism such as corpus database 350. Loader 345 may store input data processed by various components of parser 342 as documents 352.

Corpus database 350 may include raw input data stored as documents 352 and configurations to label documents as configs 351.

Configs 351 may include configuration parameters to determine labels to associate with documents 352 and generate insights of interaction content in documents 352. Configs 351 may include a configuration file sent over a network. Configs 351 may include flat files in an unstructured format as text files or semi-structured XML or JSON files. In some embodiments, configs 351 may include parsed content from a configuration file. Configs 351 may store parsed content as database tables.

Mining repository 346 may include various configurations and definitions for extracting relevant parts from input data to store in corpus database 350. Mining repository 346 may include annotation tasks 347 and ML models 348 to define and assign labels to content in documents 352.

Annotation tasks 347 include definitions of annotations to add as labels to documents 352. A user of data normalization engine 320 may provide definitions of annotations as part of a configuration file (e.g., configs 351).

ML Models 348 may include machine learning models trained by interaction miner 323 using ML model platform 325. ML models 348 may be trained using training data in corpus database 350. ML models 348 may be configured using configs 351 and set up for training using annotation tasks 347. Annotations identified using annotation tasks 347 may be used as training data for ML models 348.

In various embodiments, corpus database 350, mining repository 346, and multi-source data 101 may take several different forms. For example, mining repository 346 may be an SQL or NoSQL database, such as those developed by MICROSOFT™, REDIS, ORACLE™ CASSANDRA, MYSQL, various other types of databases, data returned by calling a web service, data returned by calling a computational function, sensor data, IoT devices, or various other data sources. Corpus database 350 may store data that is used during the operation of applications, such as interaction miner 323. In some embodiments, corpus database 130 and mining repository 140 may be fed data from an external source, or the external source (e.g., server, database, sensors, IoT devices, etc.) may be a replacement. In some embodiments, corpus database 350 may be data storage for a distributed data processing system (e.g., Hadoop Distributed File System, Google File System, ClusterFS, or OneFS). Depending on the specific embodiment of corpus database 350, interaction miner 323 may optimize the label data for storing and retrieving in corpus database 350 for optimal query performance.

Figure 4:
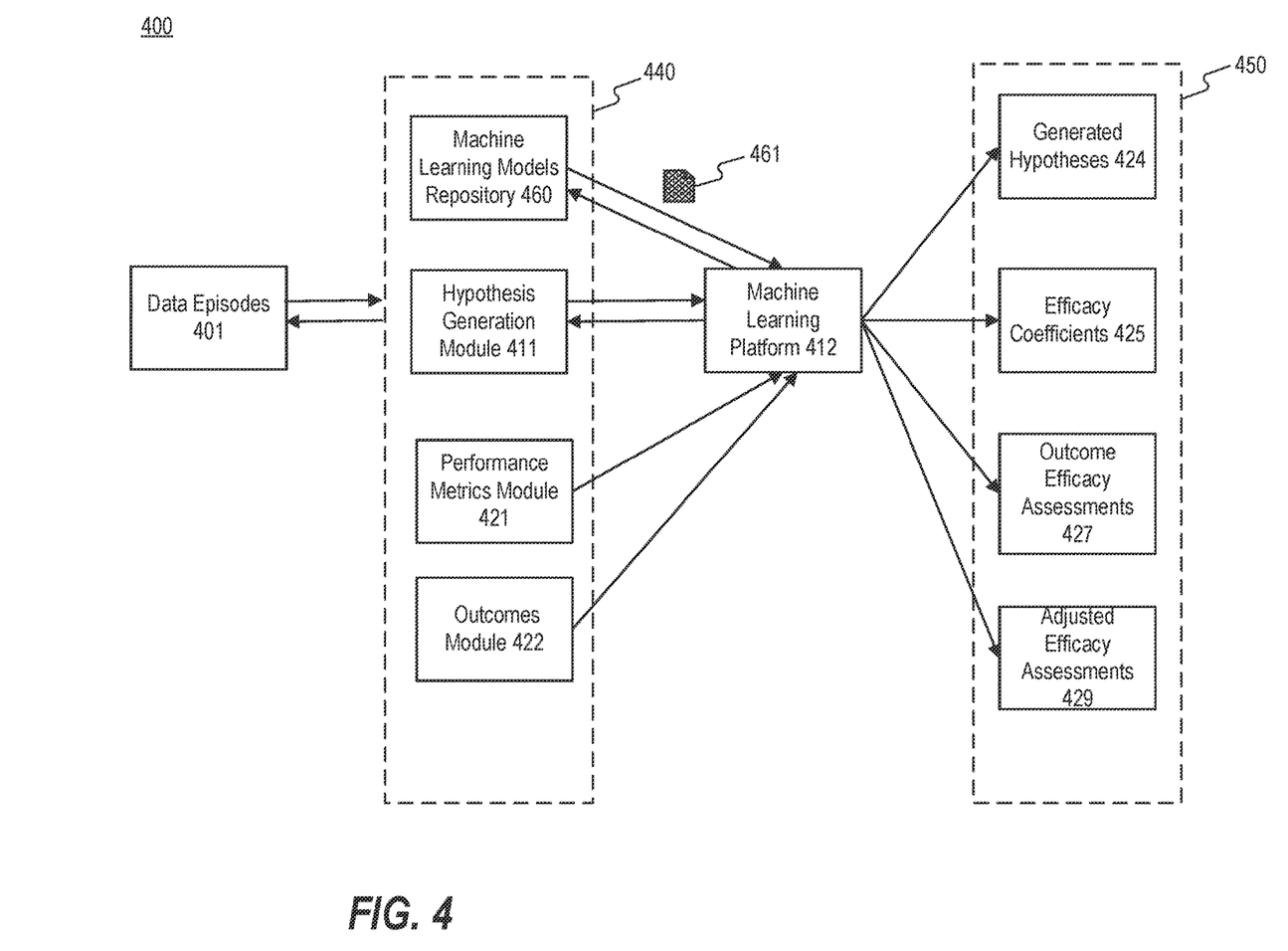
FIG. 4 is a block diagram illustrating various exemplary components of a machine learning platform, according to some embodiments of the present disclosure.

FIG. 4 is a block diagram illustrating various exemplary components of a machine learning platform, according to some embodiments of the present disclosure.

As illustrated in FIG. 4, Machine Learning (ML) Platform 412 may take as input on data from data episodes 401. ML platform 412 may generate one or more hypotheses 424 based on the data from data episodes 401 and hypothesis generation module 411. ML platform 412 may generate one or more hypotheses 424 based on one or more ML models in Machine Learning (ML) models repository 460. A ML model in ML models repository 460 may be based on one or more ML algorithms. In some embodiments, the ML algorithms may include, for example, Viterbi algorithms, Naïve Bayes algorithms, neural networks, etc. or joint dimensionality reduction techniques (e.g., cluster canonical correlation analysis, partial least squares, bilinear models, cross-modal factor analysis).

ML platform 412 may take as input a set of outcomes based on outcomes module 422. ML platform 412 may also take as input a set of performance metrics from performance metrics module 421. In some embodiments, performance metrics module 421 may directly supply performance metrics by querying an external database. In some embodiments, outcomes module 422 may directly supply one or more outcomes by querying an external database. In some embodiments, one or more ML models 461 from ML models repository 460 may be configured in ML platform 412 to observe relationships between the set of observations or events associated with one or more data episodes 401 and attributes and patterns associated with one or more outcomes based on outcomes module 422. In some embodiments, the ML models 461 may be configured in ML platform 412 to generate a set of efficacy coefficients 425 based on one or more performance metrics from performance metrics module 421 and one or more outcomes from outcomes module 422. In some embodiments, ML platform 412 may generate an efficacy assessment 427 for one or more outcomes supplied by the outcomes module 422. In some embodiments, the efficacy assessment 427 for each outcome may be in the form of a numerical score or percentage. In some embodiments, ML platform 412 may determine an adjusted efficacy assessment 429 for one or more outcomes based on the efficacy coefficients 425.

In some embodiments, ML platform 412 may link the generated hypotheses 424 with the efficacy coefficients 425, outcome efficacy assessments 427, or the adjusted efficacy assessments 429. The relationships among the generated hypotheses 424 and the efficacy coefficients and assessments (e.g., 425, 427, and 429) may be stored in a data warehouse.

In some embodiments, ML platform 412 may also store relationships between data episodes 401 and performance metrics from Performance Metrics Module 421 or outcomes from Outcomes Module 422 in a data warehouse.

In some embodiments, the at least one ML model 461 may also be trained, for example, using a supervised learning method (e.g., gradient descent or stochastic gradient descent optimization methods). In some embodiments, the ML models may be trained based on user-generated training data or automatically generated markup data. In some embodiments, one or more ML models may be configured to perform hypothesis refinement by generating an alternative hypothesis based on the efficacy coefficients 425, outcome efficacy assessments 427, or adjusted efficacy assessments 429. In some embodiments, the ML models may generate an alternative hypothesis comprising a set of observations or events associated the data episodes 401 which is distinct from the set of observations or events comprising the original hypothesis. In some embodiments, ML platform 412 may generate ML models as part of hypothesis generation by hypothesis generation module 421. ML platform 412 may store the generated ML models in ML models repository 460. ML platform 412 may generate new ML models by adjusting ML model 461 based on the efficacy coefficients, outcome efficacy assessments 427, or adjusted efficacy assessment 429.

Figure 5:
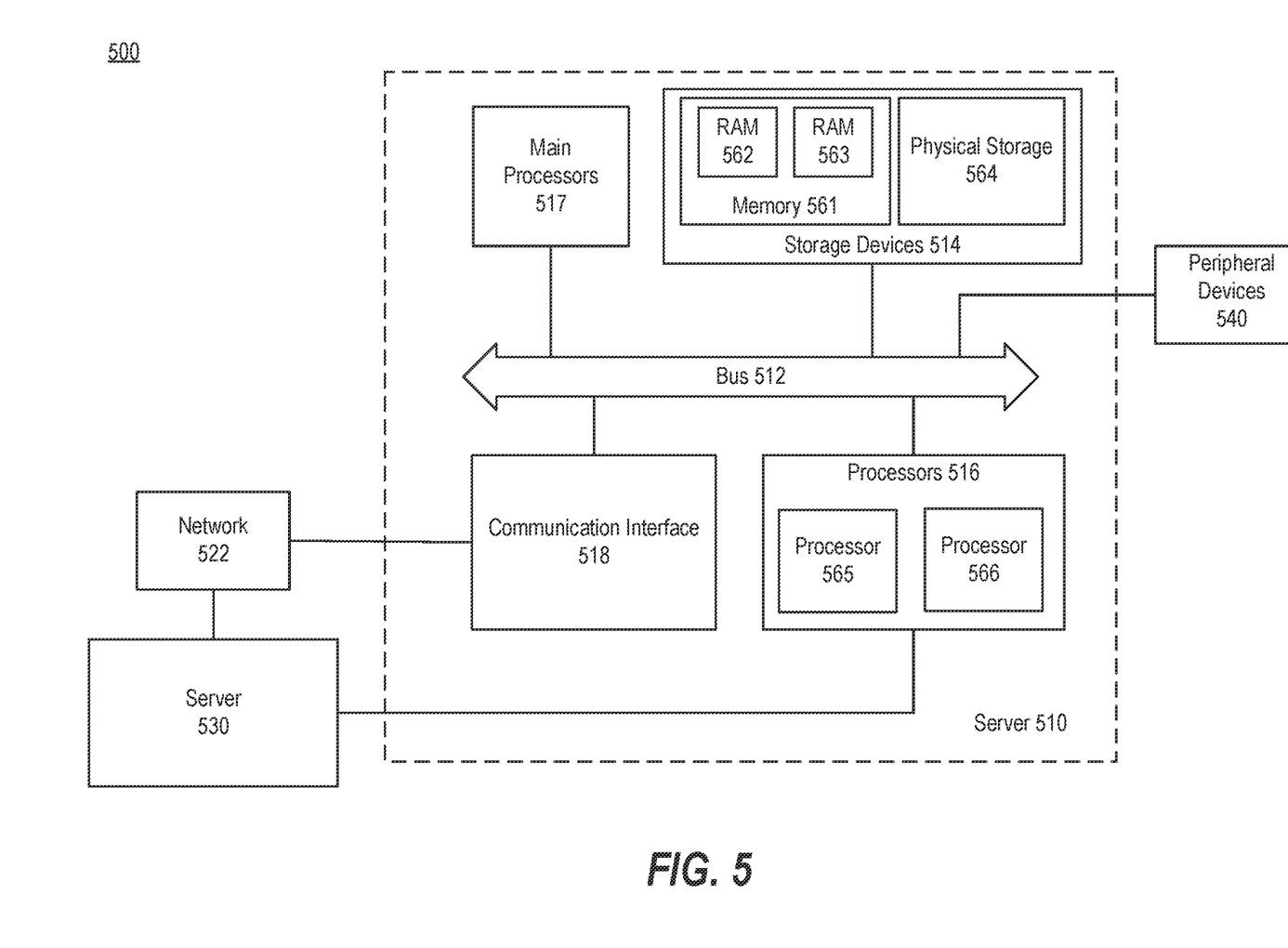
FIG. 5 illustrates a schematic diagram of an exemplary server of a distributed system, according to some embodiments of the present disclosure.

FIG. 5 illustrates a schematic diagram of an exemplary server of a distributed system, according to some embodiments of the present disclosure. According to FIG. 5, server 510 of distributed computing system 500 comprises a bus 512 or other communication mechanisms for communicating information, one or more processors 516 communicatively coupled with bus 512 for processing information, and one or more main processors 517 communicatively coupled with bus 512 for processing information. Processors 516 can be, for example, one or more microprocessors. In some embodiments, one or more processors 516 comprises processor 565 and processor 566, and processor 565 and processor 566 are connected via an inter-chip interconnect of an interconnect topology. Main processors 517 can be, for example, central processing units ("CPUs").

Server 510 can transmit data to or communicate with another server 530 through a network 522. Network 522 can be a local network, an internet service provider, Internet, or any combination thereof. Communication interface 518 of server 510 is connected to network 522, which can enable communication with server 430. In addition, server 510 can be coupled via bus 512 to peripheral devices 540, which comprises displays (e.g., cathode ray tube (CRT), liquid crystal display (LCD), touch screen, etc.) and input devices (e.g., keyboard, mouse, soft keypad, etc.).

Server 510 can be implemented using customized hardwired logic, one or more ASICs or FPGAs, firmware, or program logic that in combination with the server causes server 510 to be a special-purpose machine.

Server 510 further comprises storage devices 514, which may include memory 561 and physical storage 564 (e.g., hard drive, solid-state drive, etc.). Memory 561 may include random access memory (RAM) 562 and read-only memory (ROM) 563. Storage devices 514 can be communicatively coupled with processors 516 and main processors 517 via bus 512. Storage devices 514 may include a main memory, which can be used for storing temporary variables or other intermediate information during execution of instructions to be executed by processors 516 and main processors 517. Such instructions, after being stored in non-transitory storage media accessible to processors 516 and main processors 517, render server 510 into a special-purpose machine that is customized to perform operations specified in the instructions. The term "non-transitory media" as used herein refers to any non-transitory media storing data or instructions that cause a machine to operate in a specific fashion. Such non-transitory media can comprise non-volatile media or volatile media. Non-transitory media include, for example, optical or magnetic disks, dynamic memory, a floppy disk, a flexible disk, hard disk, solid state drive, magnetic tape, or any other magnetic data storage medium, a CD-ROM, any other optical data storage medium, any physical medium with patterns of holes, a RAM, a PROM, and an EPROM, a FLASH-EPROM, NVRAM, flash memory, register, cache, any other memory chip or cartridge, and networked versions of the same.

Various forms of media can be involved in carrying one or more sequences of one or more instructions to processors 516 or main processors 517 for execution. For example, the instructions can initially be carried out on a magnetic disk or solid-state drive of a remote computer. The remote computer can load the instructions into its dynamic memory and send the instructions over a telephone line using a modem. A modem local to server 510 can receive the data on the telephone line and use an infra-red transmitter to convert the data to an infra-red signal. An infra-red detector can receive the data carried in the infra-red signal, and appropriate circuitry can place the data on bus 512. Bus 512 carries the data to the main memory within storage devices 514, from which processors 516 or main processors 517 retrieves and executes the instructions.

Data Episode System 101 or one or more of its components may reside on either server 510 or 530 and may be executed by processors 516 or 517. In some embodiments, the components of system 100 may be spread across multiple servers 510 and 530. For example, Segmentation Engine 202 may be executed on multiple servers. Similarly, Relevance Engine 203 or Personalized Recommendation Engine 215 may be maintained by multiple servers 510 and 530.

Figure 6:
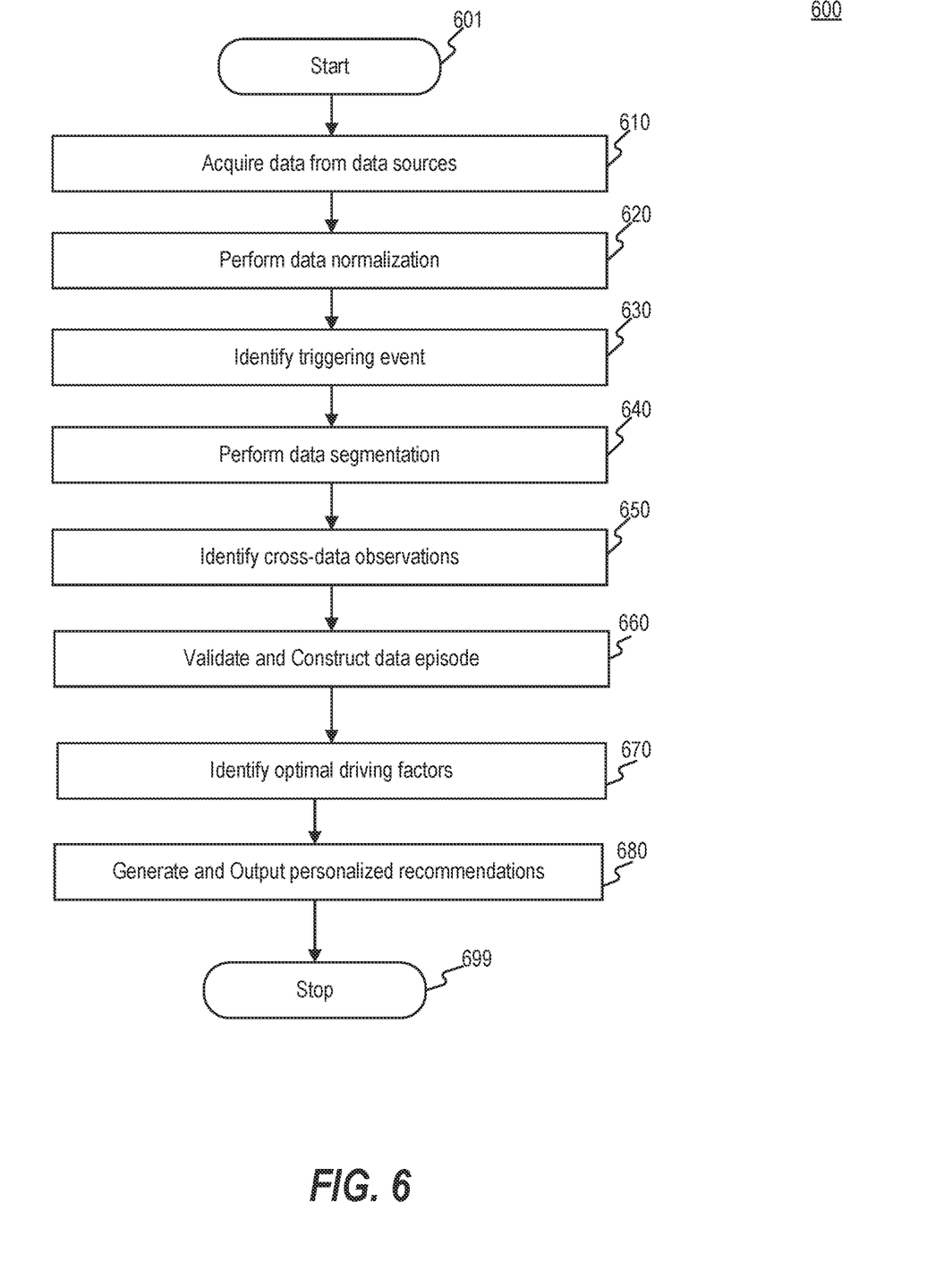
FIG. 6 is a flow diagram illustrating an exemplary process for constructing data episodes based on multi-source data, identifying optimal driving factors, and outputting personalized recommendations, according to some embodiments of the present disclosure.

FIG. 6 is a flow diagram illustrating an exemplary process 600 for constructing data episodes based on multi-source data, identify optimal driving factors, and output personalized recommendations, according to some embodiments of the present disclosure. Process 600 can be performed by a system, such as system 100 of FIG. 1. In some embodiments, process 600 can be implemented using one or more instructions that can be stored on a computer readable medium (e.g., storage device 514 of FIG. 5).

In some embodiments, process 600 begins at step 610. In step 610, the system may acquire data from one or more data sources using one or more processors. The system may perform synthesis of data across multiple data sources. In some embodiments, the system may synthesize data into collections of canonical tables. The system may also synthesize data by capturing data from additional data sources.

Process 600 then proceeds to step 620. In step 620, the system may perform data normalization of the synthesized data using one or more processors. In some embodiments, the system may normalize data based on natural language processing modules, including, but not limited to a labelling module, or a data processing module. Process 600 may perform data normalization based on one or more corpus databases. The system may perform data normalization based on a machine learning platform. In some embodiments, the system may perform data normalization based on an engine as exemplified by data normalization engine 320 in FIG. 3B.

Process 600 then proceeds to step 630. In step 630, the system may identify one or more trigger events using one or more processors. In some embodiments, the system may identify a trigger event based on one or more data events or data points defined across one or more data sources. For instance, in a healthcare setting, a trigger event may comprise of, but is not limited to, an event at a specific point in time, such as a search for a new provider physician, a search for a concierge referral, a clinical visit, or a telephonic encounter for medical care.

Process 600 then proceeds to step 640. In step 640, the system may segment the synthesized data from multiple data sources using one or more processors. The system may segment the synthesized data into one or more data collections. The system may segment the data based on one or more pre-defined trigger events. In some embodiments, the system may perform data segmentation by selecting, within the synthesized data, one or more data collections within a specific timespan associated with the trigger event. In some embodiments, the system may select data within a specific timespan based on the time stamp of the trigger event. In some embodiments, the system may perform data segmentation refinement. In some embodiments, the system may refine data segments by performing a segmentation of the synthesized data which is different from the previous data segmentation of the synthesized data.

Process 600 then proceeds to step 650. In step 650, the system may identify a set of observations or events across multiple data sources which may be relevant to a segmented data collection based on a trigger event, using one or more processors. For instance, in a health care setting, if the trigger event comprises a patient who is seeking to undergo knee surgery, an observation or event could comprise, but is not limited, to individualized recommendations of knee surgeons to the patient based on his/her medical needs or insurance coverage, previous claims or episodes of care associated with the patient, past outreach efforts to the patient with regard to appointment adherence or healthcare education, telephonic patient encounters or emergency medical encounters relating to previous knee-related symptoms. In some embodiments, the system may identify the set of observations or events based on a relevancy metric. In some embodiments, the relevancy metric may comprise of the time proximity of the observation or event to the trigger event associated with the segmented data collection. In some embodiments, the relevancy metric may comprise of the similarity between the category or type of the observation or event to the trigger event. In some embodiments, the relevancy metric may comprise of the similarity between one or more outcomes associated with the observation or event to the one or more outcomes associated with the trigger event.

Process 600 then proceeds to step 660. In step 660, the system may validate the segmented data collection by measuring the efficacy of a segmented data collection using one or more processors. In some embodiments, the system may perform an efficacy measurement based on an efficacy metric. In some embodiments, an efficacy metric may be based on a sufficiency value of the number of data events within the segmented data collection. In some embodiments, an efficacy metric may be based on the time proximity of the data events within the segmented data collection. In some embodiments, an efficacy metric may be based on the type of trigger event associated with the segmented data collection. In some embodiments, if the system determines that the efficacy of a segmented data collection is below a specific threshold value, it may transmit instructions to a data segmentation engine 103 to perform a data segmentation refinement using one or more processors. In some embodiments, the data segmentation refinement may be exemplified by 106. In some embodiments, the system may measure the efficacy of the refined segmented data collection using one or more processors. In some embodiments, the system may perform iterative cycles of data segmentation refinement and efficacy measurement until the measured efficacy of the refined data segmentation reaches a specific threshold value, using one or more processors.

Also in step 660, the system may aggregate the trigger event and the set of observations or events associated with a segmented data collection into a data episode, using one or more processors. In some embodiments, a data episode comprises of a trigger event and a set of observations or events associated with the trigger event based on a determination by the data relevance engine 104. In some embodiments, the system may transmit data episodes to a machine learning engine for additional analysis.

In some embodiments, the process can further comprise pre-training the machine learning engine (e.g., machine learning engine 214 in FIG. 2). In some embodiments, pre-training the machine learning engine may be performed by machine learning training engine 310, exemplified in FIG. 3A.

Process 600 then moves to step 670. In step 670, the system may determine a set of optimal driving factors associated with the one or more measured outcomes using one or more processors. The system may determine the set of optimal driving factors based on the set of observations or events associated with an optimal hypothesis. The optimal hypothesis may be generated by machine learning training engine 310 as exemplified in FIG. 3A.

Process 600 then moves to step 680. In step 680, the system may generate recommendations based on a set of optimal driving factors using one or more processors. For instance, in a healthcare setting, the system may determine that the set of optimal driving factors which are associated with one or more desired outcomes comprises healthcare outreach efforts targeted toward the patient (e.g., via email or online patient portal). Accordingly, the system may generate recommendations based on this optimal driving factor to increase the frequency or types of outreach efforts toward the patient. In some embodiments, the generated recommendations may be personalized to target specific users of the system. In some embodiments, the generated recommendations are based on one or more desired outcomes from the set of measured outcomes.

Also in step 680, the system may output generated recommendations through one or more output channels. In some embodiments, the system may output recommendations via digital media as exemplified by a web interface or a mobile phone interface. The system may also output recommendations through telephone calls or printed personalized informational materials to the user.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

Example embodiments are described above with reference to flowchart illustrations or block diagrams of methods, apparatus (systems) and computer program products. It will be understood that each block of the flowchart illustrations or block diagrams, and combinations of blocks in the flowchart illustrations or block diagrams, can be implemented by computer program product or instructions on a computer program product. These computer program instructions may be provided to a processor of a computer, or other programmable data processing apparatus to produce a machine, such that the instructions, which execute via the processor of the computer or other programmable data processing apparatus, create means for implementing the functions/acts specified in the flowchart or block diagram block or blocks.

These computer program instructions may also be stored in a computer readable medium that can direct one or more hardware processors of a computer, other programmable data processing apparatus, or other devices to function in a particular manner, such that the instructions stored in the computer readable medium form an article of manufacture including instructions that implement the function/act specified in the flowchart or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions that execute on the computer or other programmable apparatus provide processes for implementing the functions/acts specified in the flowchart or block diagram block or blocks.

Any combination of one or more computer readable medium(s) may be utilized. The computer readable medium may be a non-transitory computer readable storage medium. In the context of this document, a computer readable storage medium may be any tangible medium that can contain or store a program for use by or in connection with an instruction execution system, apparatus, or device.

Program code embodied on a computer readable medium may be transmitted using any appropriate medium, including but not limited to wireless, wireline, optical fiber cable, RF, IR, etc., or any suitable combination of the foregoing.

Computer program code for carrying out operations, for example, embodiments may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowchart and block diagrams in the figures illustrate examples of the architecture, functionality, and operation of possible implementations of systems, methods, and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

It is understood that the described embodiments are not mutually exclusive, and elements, components, materials, or steps described in connection with one example embodiment may be combined with, or eliminated from, other embodiments in suitable ways to accomplish desired design objectives.

In the foregoing specification, embodiments have been described with reference to numerous specific details that can vary from implementation to implementation. Certain adaptations and modifications of the described embodiments can be made. Other embodiments can be apparent to those skilled in the art from consideration of the specification and practice of the invention disclosed herein. It is intended that the specification and examples be considered as exemplary only. It is also intended that the sequence of steps shown in figures are only for illustrative purposes and are not intended to be limited to any particular sequence of steps. As such, those skilled in the art can appreciate that these steps can be performed in a different order while implementing the same method.

What is claimed is:

1. A non-transitory computer readable medium including instructions that are executable by one or more processors to cause a system to perform a method for multi-domain data segmentation, and automatically generating and refining hypotheses, the method comprising:
    receiving multi-domain data from a plurality of data sources;
    normalizing the multi-domain data;
    identifying a trigger event based on the normalized data;
    generating an episode based on a segmentation of the normalized data and the trigger event;
    identifying at least one set of observations associated with the episode based on the normalized data and one or more relevancy metrics, whereas the one or more relevancy metrics comprises a similarity metric based on the trigger event;
    iteratively performing operations until a threshold value has been reached, wherein the operations comprise:
        generating a hypothesis based on a subset of observational features using machine learning,
        generating a measure of one or more outcomes based on one or more outcome metrics, wherein the one or more outcomes metrics comprise a provider match, a concierge referral, monetary savings, reduction in expenditure, or other product metrics, and
        validating the hypothesis based on the generated measure;
    identifying one or more driving factors for the one or more outcomes using an optimal hypothesis.

2. The non-transitory computer readable medium of claim 1, wherein the data sources comprise claims data, digital product data, telephonic data, or laboratory data.

3. The non-transitory computer readable medium of claim 1, wherein normalizing the received data further comprises capturing data.

4. The non-transitory computer readable medium of claim 1, wherein the trigger event comprises a clinical visit, a claim filing, or a telephone encounter.

5. The non-transitory computer readable medium of claim 1, wherein the instructions that are executable by one or more processors are configured to cause the system to further perform:
    determining an optimal hypothesis based on the generated hypothesis upon reaching a threshold value.

6. A non-transitory computer readable medium including instructions that are executable by one or more processors to cause a system to perform a method for multi-domain data segmentation, and automatically generating and refining hypotheses, the method comprising:
    receiving multi-domain data from a plurality of data sources;
    normalizing the multi-domain data;
    identifying a trigger event based on the normalized data;
    generating an episode based on a segmentation of the normalized data and the trigger event;
    identifying at least one set of observations associated with the episode based on the normalized data and one or more relevancy metrics, whereas the one or more relevancy metrics comprises a similarity metric based on the trigger event;
    iteratively performing operations until a threshold value has been reached, wherein the operations comprise:
        generating a hypothesis based on a subset of observational features using machine learning,
        generating a measure of one or more outcomes based on one or more outcome metrics, and
        validating the hypothesis based on the generated measure;
    identifying one or more driving factors for the one or more outcomes using an optimal hypothesis,
    generating a set of recommendations based on the identified set of driving factors, and
    outputting the recommendations through a set of outflow channels comprising customers, product and service staff, user interfaces, or digital agents.

7. A method utilized by a system for multi-domain data segmentation, automatic hypotheses generation and refinement, the method comprising:
    receiving multi-domain data from a plurality of data sources;
    normalizing the multi-domain data;
    identifying a trigger event based on the normalized data;
    generating an episode based on a segmentation of the normalized data and the trigger event;
    identifying at least one set of observations associated with the episode based on the normalized data and one or more relevancy metrics, whereas the one or more relevancy metrics comprises a similarity metric based on the trigger event;

iteratively performing operations until a threshold value has been reached, wherein the operations comprise:
  generating a hypothesis based on a subset of observational features using machine learning,
  generating a measure of one or more outcomes based on one or more outcome metrics, wherein the one or more outcomes metrics comprise a provider match, a concierge referral, monetary savings, reduction in expenditure, or other product metrics, and
  validating the hypothesis based on the generated measure;

identifying one or more driving factors for the one or more outcomes using an optimal hypothesis.

8. The method of claim 7, wherein the data sources comprise claims data, digital product data, telephonic data, or laboratory data.

9. The method of claim 7, wherein normalizing the received data further comprises capturing data.

10. The method of claim 7, wherein the trigger event comprises a clinical visit, a claim filing, or a telephone encounter.

11. The method of claim 7, further comprising determining an optimal hypothesis based on the generated hypothesis upon reaching a threshold value.

12. A method utilized by a system for multi-domain data segmentation, automatic hypotheses generation and refinement, the method comprising:

receiving multi-domain data from a plurality of data sources;

normalizing the multi-domain data;

identifying a trigger event based on the normalized data;

generating an episode based on a segmentation of the normalized data and the trigger event;

identifying at least one set of observations associated with the episode based on the normalized data and one or more relevancy metrics, whereas the one or more relevancy metrics comprises a similarity metric based on the trigger event;

iteratively performing operations until a threshold value has been reached, wherein the operations comprise:
  generating a hypothesis based on a subset of observational features using machine learning,
  generating a measure of one or more outcomes based on one or more outcome metrics, and
  validating the hypothesis based on the generated measure;

identifying one or more driving factors for the one or more outcomes using an optimal hypothesis, generating a set of recommendations based on the identified set of driving factors, and outputting the recommendations through a set of outflow channels comprising customers, product and service staff, user interfaces, or digital agents.

* * * * *